(12) United States Patent
Rittscher et al.

(10) Patent No.: US 7,940,978 B2
(45) Date of Patent: May 10, 2011

(54) AUTOMATIC CHARACTERIZATION OF CELLULAR MOTION

(75) Inventors: Jens Rittscher, Ballston Lake, NY (US); Thomas B. Sebastian, Flemington, NJ (US); Stewart E. Abbot, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 1008 days.

(21) Appl. No.: 11/758,531

(22) Filed: Jun. 5, 2007

(65) Prior Publication Data
US 2008/0304732 A1    Dec. 11, 2008

(51) Int. Cl.
G06K 9/00 (2006.01)
G01N 33/48 (2006.01)
(52) U.S. Cl. .................................. 382/133; 702/21
(58) Field of Classification Search .......... 382/128, 382/129, 130, 131, 132, 133, 134; 600/407, 600/410, 476, 562; 435/29, 820; 436/63, 436/519; 702/21
See application file for complete search history.

(56) References Cited

U.S. PATENT DOCUMENTS

| | | | |
|---|---|---|---|
| 5,411,883 A * | 5/1995 | Boss et al. | 435/29 |
| 5,783,408 A * | 7/1998 | Hamilton et al. | 435/29 |
| 7,115,256 B1 * | 10/2006 | Allen et al. | 424/93.1 |
| 7,678,051 B2 * | 3/2010 | Fan et al. | 600/438 |
| 2003/0185450 A1 | 10/2003 | Garakani et al. | |
| 2005/0226484 A1 | 10/2005 | Basu et al. | |
| 2006/0097175 A1 | 5/2006 | Ganin et al. | |
| 2007/0031028 A1 | 2/2007 | Vetter et al. | |
| 2007/0042044 A1 | 2/2007 | Fischer et al. | |
| 2007/0073159 A1 | 3/2007 | Ehben et al. | |
| 2007/0083123 A1 | 4/2007 | Ehben et al. | |
| 2007/0083124 A1 | 4/2007 | Ehben et al. | |
| 2007/0086635 A1 | 4/2007 | Fink et al. | |
| 2007/0109874 A1 | 5/2007 | Padfield et al. | |

OTHER PUBLICATIONS

Padfield, D.R. et al.: "Spatio-Temporal Cell Cycle Analysis Using 3D Level Set Segmentation of Unstained Nuclei in Line Scan Confocal Fluorescence Images", Biomedical Imaging: Macro to Nano, 2006, 3rd IEEE International Symposium on Apr. 6, 2006, pp. 1036-1039.

* cited by examiner

Primary Examiner — Abolfazl Tabatabai
(74) Attorney, Agent, or Firm — Fletcher Yoder (57) ABSTRACT

The present techniques provide for the evaluation of cellular motion and/or cellular properties based on an analysis of motion. In an exemplary technique, images of one or more cells are acquired and motion data for the one or more cells is derived from the images. The motion data is decomposed to generate one or more motion components. The one or more motion components can be used to evaluate cellular properties and/or cellular motion properties.

32 Claims, 4 Drawing Sheets

AUTOMATIC CHARACTERIZATION OF CELLULAR MOTION

BACKGROUND

The present techniques relate generally to the evaluation and assessment of cellular cultures, tissues and organisms which may be used to assess pharmacological effects. In particular, the present techniques relate to the use of visual motion analysis in the evaluation and assessment of cellular motion.

The focus of the pharmaceutical industry is typically to develop new and medically useful drugs that are effective at treating a disease or disorder of a patient. In addition, it is generally desirable that such new and useful drugs have few or no adverse side effects. However, as should be apparent, the number of compounds that might be useful as drugs far exceeds the number that will ultimately be developed. As a result, the pharmaceutical industry screens vast numbers of drug candidates in an attempt to select those few that warrant additional testing and development.

One such screening technique utilizes simple living system based assessment, e.g. cell assays, to determine the effect of a compound on one or more characteristics of a cell culture. Such cell assays are relatively inexpensive compared to in-vivo animal studies and therefore provide a cost effective way to perform large-scale screening of compounds. In particular, a typical cell assay may involve applying a compound of interest to a cell culture and subsequently evaluating one or more characteristics of the cells forming the culture. Based upon the evaluation of the characteristics, the effect of the compound may be evaluated.

In some instances, however, it may be difficult to assess the effect of the compound on the characteristic of interest. For example, in some instances, the characteristic of interest may not be attributable to a single cell but may instead be a characteristic of a group of cells. One example of such a characteristic is the coordinated motion of cells, such as cardiac cells, that may correspond to the rhythmic or periodic motion of a corresponding organ, such as the beating of a heart.

Currently, however, there is no way to effectively assess such coordinated motion in a quick, objective, and reproducible manner. For example, one current technique for assessing treatment effects on coordinated cellular motion involves having an observer watch a video of the cell culture after treatment with a compound and make an assessment of the effect of the compound on the coordinated motion of the cells. Such observer based analysis, however, is subjective, slow, and generally not reproducible.

Alternatively, aggregate area measurements of one or more electrical properties of the cells of the culture may be made and, based upon changes in the one or more electrical properties, an assessment of the effect of the compound on the motion of the cells may be made. Such electrophysiological assays, however, may be problematic due to the technical difficulty involved in performing the assay as well as to relatively low throughput which may be unsuitable for mass screenings. Further, there may be a poor correlation between the aggregate electrical measurements and the cellular motion. In addition, to the extent that the characteristic of interest is coordinated motion, not simply cellular motion in general, such aggregate electrical measurements may not be useful in assessing the coordinated nature of the cellular motion.

It is, therefore, desirable to be able to more effectively assess certain cellular characteristics, such as characteristics associated with cellular motion, when determining the effect of a compound on the cells.

BRIEF DESCRIPTION

In accordance with the present technique, motion data is derived from images of one or more cells. The motion data is decomposed, such as using a factorization technique, to generate one or more motion components that, in certain implementations, provide a lower dimensional representation of the motion data that may be easier to analyze. The one or more motion components may then be used to evaluate the properties or motion of the one or more cells, such as by performing a time-based analysis, such as a time series analysis, on the one or more motion components. Based on the evaluation of the cells, an effect of a treatment administered to the cells may be evaluated and/or the state of some or all of the cells may be determined.

In one aspect of the present technique, a method is provided for evaluating cellular motion and/or properties. This method includes the act of acquiring a plurality of images of one or more cells. Motion data for the one or more cells is derived from the plurality of images. The motion data is decomposed to generate one or more motion components. At least one of cellular motion properties or cellular properties is evaluated, based on the one or more motion components.

In a further aspect of the present technique, a computer program is provided on one or more computer-readable media. The computer program includes a routine configured to derive motion data for one or more cells from a plurality of images. In addition the computer program includes a routine configured to decompose the motion data to generate one or more motion components. Further, the computer program includes a routine configured to evaluate at least one of cellular motion properties or cellular properties based on the one or more motion components.

In an additional aspect of the present technique, an image analysis system is provided. The image analysis system includes an imager configured to optically scan one or more cells and data acquisition circuitry configured to acquire images of the one or more cells via the imager. The image analysis system also includes data processing circuitry configured to derive motion data for the respective one or more cells from the images. The data processing circuitry is also configured to decompose the motion data to generate one or more motion components. In addition, the data processing circuitry is configured to evaluate at least one of cellular motion properties or cellular properties based on the one or more motion components.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present technique is directed to the high-throughput screening of treated and/or untreated cell cultures using automated or semi-automated optical methods. For example, in an exemplary embodiment, the present technique may be utilized to assess treatment effects of compounds on cellular motion, thereby potentially providing insight into the effect of a compound on the motion or coordination of motion of treated cells. In such an example, a high-throughput microscope may be employed to obtain a video of a treated collection of cells. Frames of the video may be analyzed in a sequential order using optical techniques to generate motion data representing cellular motion over time. The motion data may in turn be analyzed to determine the effect of a treatment on cellular motion. For example, in one embodiment, the motion data may be decomposed into motion components, such as primary motion components, secondary motion components, and so forth, which may be used to determine treatment effects.

In this manner, cellular motion may be used in the evaluation of different treatments or environmental factors where effects on cellular motion may be expected. For example, the techniques discussed herein may be useful in evaluating drug candidates for effects on the cardiac cycle, such as for the potential to induce arrythmias. In such a screening context, the various candidate compounds may be evaluated for their effects on the QT interval or other recognized heart cycle interval of interest. For example, drug candidates may be screened to assess whether they prolong the QT interval, which has been theorized as being linked to arrhythmiogenesis. In such an implementation, the candidate compounds may be assayed to determine their effects on sheets or panels of mature cardiomyocytes which, untreated, would move in a coordinated, rhythmic manner at a given frequency. Compounds that alter the rhythmic motion of the cardiomyocytes, either by causing the frequency of the rhythmic motion to increase or decrease or by disrupting the coordination of the motion, may warrant further scrutiny for potential effects on the cardiac cycle.

Alternatively, in other embodiments, instead of determining treatment effects, the motion data, or a subsequent analysis of the motion data, may be used to determine the state (such as the maturity, viability, differentiation status, activation status, and so forth) of constituent cells of the respective cell cultures based upon their motion characteristics. For example, cell cultures exhibiting coordinated motion may be graded as mature while cell cultures that do not exhibit coordinated motion may be graded as immature. Likewise, in some embodiments, such maturity grading may be used to segment the cell culture. For example, the motion data or the analysis of the motion data may be used to distinguish or segment portions of a cell culture, such as of cardiomyocytes, that are mature and move in a coordinated manner from those portions that are immature and do not move in a coordinated manner. Based on the segmentation, a differential treatment or analysis may be applied such that mature cells are treated or analyzed in one manner while immature cells are treated or analyzed in a different manner.

Figure 1:
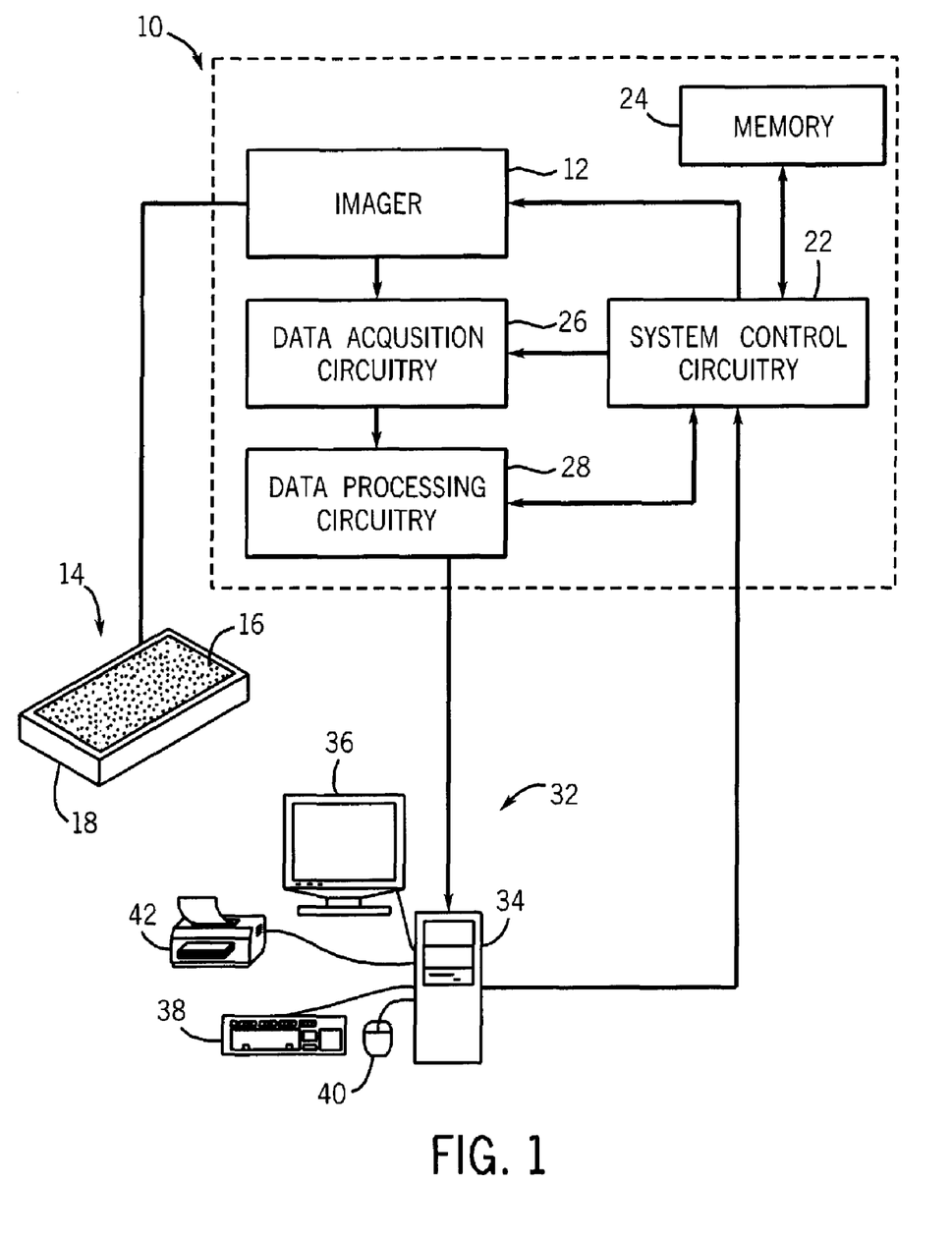
FIG. 1 is a diagrammatical view of an exemplary system for use in acquiring image data of cells, in accordance with aspects of the present technique.

With the foregoing in mind, an exemplary imaging system 10 capable of operating in accordance with the present technique is depicted in FIG. 1. Generally, the imaging system 10 includes an imager 12 that detects signals and converts the signals to data that may be processed by downstream processors. As described more fully below, the imager 12 may operate in accordance with various physical principles, such as optical principles, for creating the image data. In general, the imager 12 generates image data, of any dimension, in a conventional medium, such as photographic film, or in a digital medium. For example, in some embodiments the imager 12 may generate one or a limited numbers of lines or partial lines of image data, i.e., substantially one-dimensional image data. In other embodiments, the imager 12 may generate substantially two-dimensional image data encompassing an area, i.e., a circular, square, rectangular, or similar area. Furthermore, in one embodiment, the imager 12 may provide some degree of magnification while in other embodiments the imager 12 provides little or no magnification. For example, in one implementation, the imager 12 may be a microscope, such as a high-throughput microscope, suitable for image and/or video acquisition under magnification at suitable light wavelengths (such as visible, infrared, and/or ultraviolet light wavelengths). For example, the imager 12 may be any suitable imaging device, including a line scan camera, a fluorescence microscope, a confocal fluorescence microscope, a laser scanning confocal microscope, or a total internal reflection fluorescence microscope.

In the depicted embodiment, the imager 12 is configured to image a cell culture 14, such as a culture of myocytes or other suitable cells 16, grown on a slab 18 of suitable culture media, such as a 100 μm×100 μm slab of culture media, under suitable culture conditions, such as at 37° C. and 5% $CO_2$. While such a collection of cells (a slab) is one possible medium upon which the one or more cells 16 can be provided, the one or more cells 16 may alternatively be provided or grown on other sizes or configurations of media and may, in some implementations, be provided as a volume for analysis. The cell culture 14 will typically be of a cell type and maturity suitable for performing a desired assay or for otherwise assessing a desired treatment effect. In some embodiments, the cell culture 14 may include progenitor cells or other cells which are matured or grown into the desired cell type, such as myocytes. In such embodiments, as discussed below, an aspect of the present technique may involve assessing the state (i.e., the maturity, viability, differentiation status, activation status, and so forth) of the progenitor or mature cells and/or segregating image data acquired of the culture 14 based on the determined state of the cells 16.

In one embodiment, the imager 12 operates under the control of system control circuitry 22. The system control circuitry 22 may include a wide range of circuits, such as circuitry controlling the emission of various types of electromagnetic radiation (such as visible, infrared, and/or ultraviolet light, X-rays, electron beams, and so forth) for use in the imaging process. Likewise, in some embodiments, the system control circuitry 22 may include timing circuitry, circuitry for coordinating data acquisition in conjunction with movement of a sample, circuitry for controlling the position of the imager 12 and/or the samples undergoing images, and so forth.

In the present context, the imaging system 10 may also include memory elements 24, such as magnetic or optical storage media, for storing programs and routines executed by the system control circuitry 22 and/or by associated components of the system 10, such as data acquisition circuitry 26 and/or data processing circuitry 28. The stored programs or routines may include programs or routines for performing all or part of the present technique.

In the depicted embodiment, data acquisition circuitry 26 is employed to acquire image data from the imager 12. In optical embodiments, the data acquisition circuitry 26 may be configured to acquire image data via one or more optical sensing elements, such as may be found in digital cameras, that are disposed on or in the imager 12. The acquired image data may be digital or analog in nature and may, in certain embodiments, represent sequential images or video composed of such sequential images. In embodiments where the initially acquired image data is analog in nature, the data acquisition circuitry 26 may also be configured to convert the analog data to a digital format. Likewise, the data acquisition circuitry 26 may be configured to provide some initial processing of the acquired image data, such as adjustment of digital dynamic ranges, smoothing or sharpening of data, as well as compiling of data streams and files, where desired.

The image data acquired by the data acquisition circuitry 26 may be processed, such as by data processing circuitry 28 in the depicted embodiment. For example, in certain embodiments, the data processing circuitry 28 may perform various transformations or analyses of the image data, such as ordering, sharpening, smoothing, feature recognition, and so forth. Prior or subsequent to processing, the image data may be stored, such as in memory elements 24 or a remote device, such as a picture archiving communication systems or workstation connected to the imaging system 10, such as via a wired or wireless network connection.

The raw or processed image data may, in some embodiments, be provided to or displayed on an operator workstation 32. In such embodiments, the operator workstation 32 may be configured to allow an operator to control and/or monitor the above-described operations and functions of the imaging system 10, such as via an interface with the system control circuitry 22. The operator workstation 32 may be provided as a general purpose or application specific computer 34. In addition to a processor, the computer 34 may also include various memory and/or storage components including magnetic and optical mass storage devices, internal memory, such as RAM chips. The memory and/or storage components may be used for storing programs and routines for performing the techniques described herein that are executed by the computer 34 or by associated components of the imaging system 10. Alternatively, the programs and routines may be stored on a computer accessible storage and/or memory remote from the computer 34 but accessible by network and/or communication interfaces present on the compute 34.

The computer 34 of the operator workstation 32 may also comprise various input/output (I/O) interfaces, as well as various network or communication interfaces. The various I/O interfaces may allow communication with user interface devices of the operator workstation 32, such as a display 36, keyboard 38, mouse 40, and/or printer 42, that may be used for viewing and inputting configuration information and/or for operating the imaging system 10. The various network and communication interfaces may allow connection to both local and wide area intranets and storage networks as well as the Internet. The various I/O and communication interfaces may utilize wires, lines, or suitable wireless interfaces, as appropriate or desired.

Though a single operator workstation 32 is depicted for simplicity, the imaging system 10 may actually be in communication with more than one such operator workstation 32. For example, an imaging scanner or station may include an operator workstation 32 used for regulating the parameters involved in the image data acquisition procedure, whereas a different operator workstation 32 may be provided for viewing and evaluating results.

For the purpose of explanation, certain functions and aspects of the present technique have been described as being separate and distinct or as being associated with certain structures or circuitry. However, such distinctions have been made strictly to simplify explanation and should not be viewed as limiting. For example, for simplicity the preceding discussion describes implementation via a discrete imaging system 10 and operator workstation 32. As will be appreciated, however, certain functions described as being performed by the imaging system 10, such as data acquisition, data processing, system control, and so forth, may instead be performed on the operator workstation 32 or may have differing aspects, some of which are performed on the imaging system 10 and others of which are performed on the operator workstation 32. Indeed, in practice, virtually all functions attributed to the imaging system 10, with the possible exception of the functions attributed to the imager 12, may be performed on an operator workstation 32. In other words, the data acquisition circuitry 26, memory 24, data processing circuitry 28, and/or system control circuitry 22 may be provided as hardware or firmware provided in an operator workstation 32 and/or as software executable by the operator workstation 32. For example, some or all of the circuitry described herein may be provided as routines executed on a suitable processor or coprocessor of a computer 34 of an operator workstation 32. Indeed, it should be understood that the term circuitry, as used herein, encompasses, dedicated or generalized hardware or firmware implementations and/or processor-executable software implementations suitable for implementing the described functionality.

Figure 2:
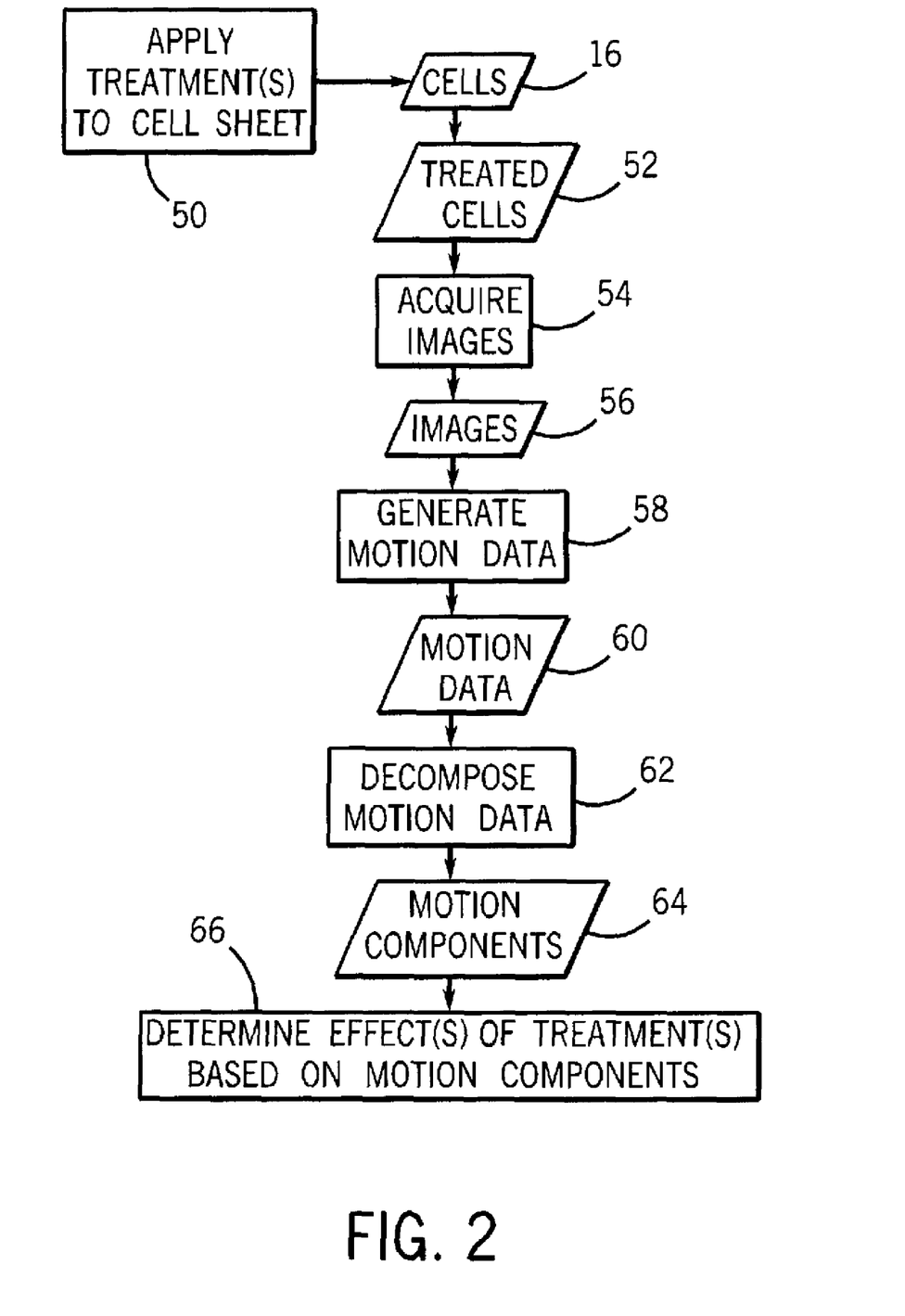
FIG. 2 is a flow chart depicting acts for determining treatment effects on cultured cells, in accordance with the present technique.

In view of the foregoing, and referring now to FIG. 2, exemplary acts illustrating one aspect of the present technique are described. In the depicted implementation, one or more cells 16 are treated (Block 50) with a desired chemical or physical stimulus to produce one or more respective treated cells 52. The cells 16 may be any appropriate cell type, including mammalian cells, human cells, immortalized cell lines, myocytes (such as cardiomyocytes), progenitor cells, and so forth. While the one or more cells 16 may be provided in vitro, i.e., as part of a cell culture 14 (FIG. 1), in some embodiments, in other embodiments, in vivo cells (such as the cells of a model organism or tissue sample) may be employed. For example, in one implementation, cells of a model organism that is conducive to internal optical inspection may be employed. One example, of such an organism is a zebra fish, which has semi-transparent characteristics, allowing internal organs, tissues, and cells to be visually observed. Other examples of potential model organisms include *Caenorhabditis elegans*, various species of the genus *Drosophila*, and so forth. In such in vivo embodiments, the model organism or organisms may be fixed in a generally transparent medium to immobilize the organisms before or after application of the desired treatment to the organisms. The internal cells, tissues, or organs of interest in the fixed organisms may then be microscopically observed.

As will be appreciated, the term "treatment" as used herein may encompass various physical or chemical stimuli applied to the cells 16. For example, a treatment may include electrical, mechanical, thermal, or other modifications to the physical environment of the cells 16. Likewise, a treatment may include application of a compound under review to the cells 16. Such a compound may be a test compound or drug candidate being reviewed for pharmacological effects or side effects. In such chemical treatment implementations, the compound administered may be any molecule, either naturally occurring or synthetic, e.g., protein, oligopeptide (e.g., from about 5 to about 25 amino acids in length), small organic molecule, polysaccharide, lipid, fatty acid, polynucleotide, oligonucleotide, etc., to be tested for effects on the cell culture 14. The test compound can be in the form of a library of test compounds, such as a combinatorial or randomized library that provides a sufficient range of compound structural diversity. Further, in some embodiments, cells may be genetically altered by "knocking out" or silencing specific genes in order to mimic different metabolic or familial cellular disorders.

Once the treated cells 52 are generated, images 56 are acquired (block 54) of the treated cells. In one embodiment, the images 56 may be sequentially acquired, such as at a give time interval (every half-second, second, two second, and so forth). Alternatively, the images 56 may be acquired as part of a video, i.e., the images 56 may be frames of a video. In one implementation, the frequency at which images 56 are generated is about twice (or greater) the frequency of the motion under observation. By way of example, if the motion of cardiomyocytes was under observation and such motion was believed to have a frequency of approximately 4 Hz, the rate at which images 56 are generated would be about 8 Hz or greater in this example, i.e., 8 frames per second or greater. In embodiments where the images 56 are acquired under magnification, such as using a high-throughput microscope, the images 56 may represent the treated cells at 2×, 4×, 8×, 16×, 32× or some other suitable magnification.

Based upon the images 56, motion data 60 may be generated (Block 58). In the depicted embodiment, the motion data 60 represents the motion of the treated cells 52 in the interval between the acquisition of the images 56 used to generate the motion data 56. In other words, the motion data 56 represents the displacement of each respective cell between images 56, such as between frames of a video. In this manner, given a sequence of images, $\{I_t\}_t$, all motion fields, $V_t$, i.e., motion data 60, are calculated on the basis of two consecutive frames or images 56, $I_t$ and $I_{t-1}$. As will be appreciated, the aggregate motion data sets 60 may include information about a variety of motion characteristics, such as motion periodicity or frequency, motion direction, motion speed and/or acceleration, and so forth. In one exemplary embodiment, the motion data 60 may be provided as a series of displacement vector diagrams indicating the presence and direction of displacement between successive images 56.

Various techniques may be applied to extract the motion data 60. In some implementations, traditional optical flow algorithms may be applied to extract the motion data 60 from the images 56. In such implementations, a constraint, such as an intensity constraint, may be employed to enforce some degree of quality control (such as regarding consistency or smoothness) on the extracted motion data 60. In other implementations, other motion extraction techniques may be employed. An example of such an alternative motion extraction technique employs deformable registration algorithms or modified versions of such algorithms to extract the motion field. Such techniques typically identify corresponding regions, such as cells or groups of cells, in successive images and based on the differences in where the regions are identified in each image, determine the translation or motion, i.e., the deformation, necessary to generate the second image from the first. In such implementation, therefore, the identified deformation between the successive images corresponds to the motion field being extracted.

Because the motion data 60 may be complex, it may be desirable to remove or reduce some of the complexity to facilitate analysis. For example, complex two or three dimensional motion data may be represented in a one or two dimensional form, respectively, to simplify analysis. This may be accomplished in various ways. For instance, in the depicted embodiment, the motion data 60 is decomposed (Block 62) to generate respective motion components 64 that may be used to evaluate or characterize the observed motion. In particular, in an exemplary embodiment, the complex and high-dimensional motion information is projected into a low-dimensional subspace to extract time series data for analysis. In an exemplary embodiment, the decomposition of the motion data 60 is accomplished via a factorization technique, such as principal component analysis (PCA) or independent component analysis (ICA). For example, in one such implementation, the principal components of the set of motion fields, i.e., $V_t$, are used to compute a projection into a low-dimensional space, such as a one or two-dimensional projection.

In this low-dimensional sub-space, the motion information can be represented as a one-dimensional data series, such as a one-dimensional time series. For example, in one implementation a respective motion field, $V_t$, may be projected onto the first principal component to calculate a scalar value $\omega_t$. The resulting time series of scalar values, i.e., $\{\omega_t\}_t$ may be analyzed to detect changes in the local frequency attributable to changes in the motion of the one or more treated cells 52. In particular, traditional linear systems theory or similar techniques useful for detecting changes in a time series of data may be employed to detect changes in the frequency of the apparent motion of the one or more treated cells 52 based upon the time series of scalar values. Therefore, in an implementation where the effect of the treatment applied at Block 50 is under investigation, the treatment effects may be determined (Block 66) based upon the motion components 64 using such an analysis of the resulting time series of data.

Figure 3:
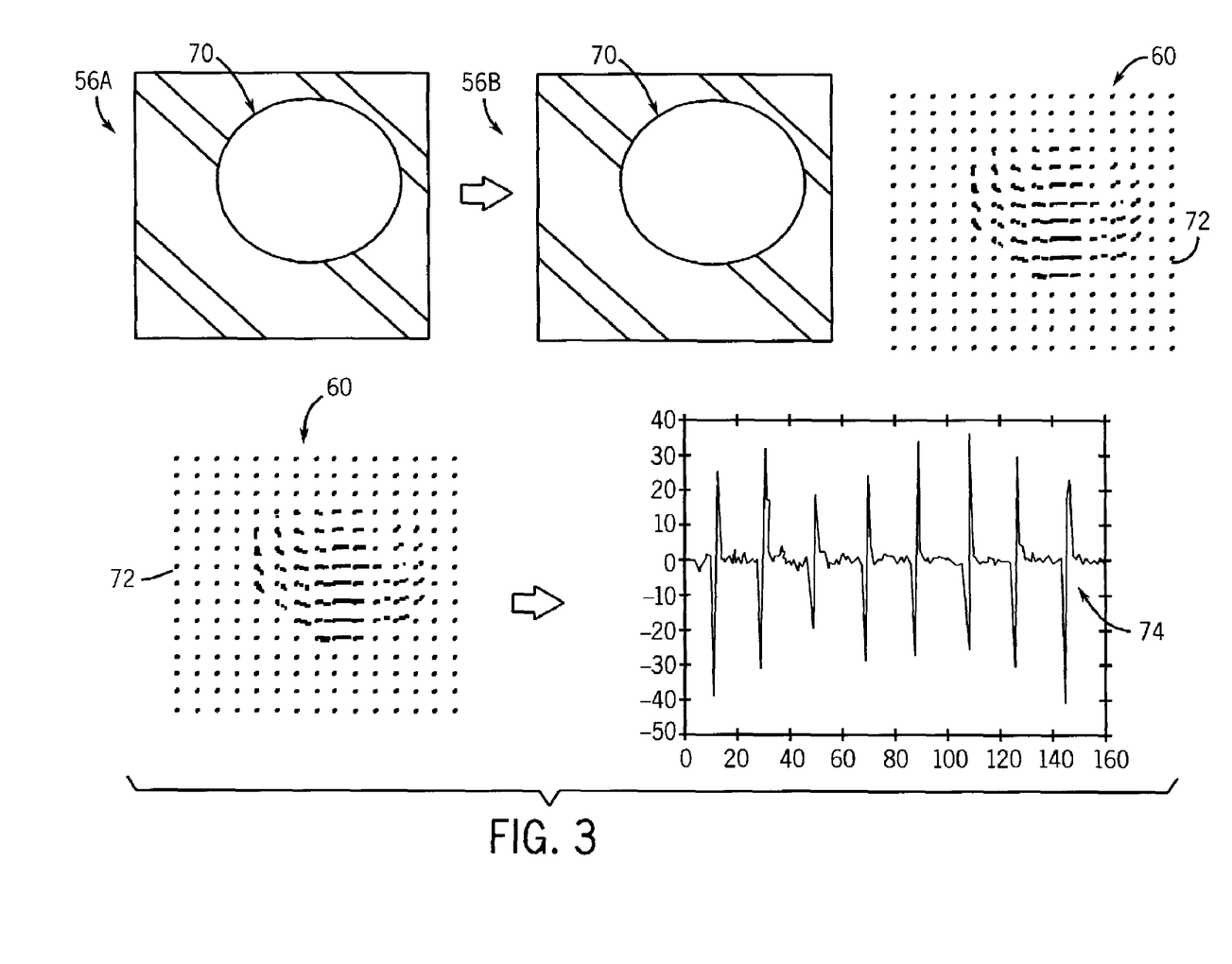
FIG. 3 is a graphical representation of certain data discussed with regard to the acts of FIG. 2, in accordance with the present technique.

A graphical example, of the above technique is provided in FIG. 3. In this example, exemplary successive images 56A and 56B of treated cells 52 are depicted. Based upon the observed differences in position of respective cells or groups of cells, in a common region of interest 70, motion data 60 is generated. In the depicted embodiment, the motion data 60 is provided as a displacement vector diagram 72 in which regions of no discernible motion between the images 56A and 56B (or where motion was not calculated) are indicated by a "+". Conversely, regions where respective cells or groups of cells have moved, i.e., where the respective cells are in different positions in the respective images 56A and 56B, are indicated by a respective arrow, with the direction the arrow points indicating the vector of the respective cell motion.

In the depicted example, the motion data 60 representing the motion between images 56, such as the respective displacement vector diagrams 72 representing the motion between each successive image pair 56A and 56B, is decomposed, such as by PCA or ICA, allowing projection into a low dimensional sub-space. In this manner, the vector fields present in the displacement vector diagrams 72 may be analyzed with respect to the main mode of variation, i.e., the first principal component or first independent component. In the depicted embodiment, the decomposed motion data 60 is presented as a one-dimensional time series, here depicted as a waveform 74. Such a waveform 74 may be easily evaluated or analyzed using conventional techniques for detecting changes in a time series to assess treatment effects or some other factor believed to be related to cellular motion.

For example, in one embodiment employing PCA the motion, M, at time, t, may be characterized as:

$$M_t \sim a_t * PC_1 + B_t * PC_2 \qquad (1)$$

where first and second principal components, $PC_1$ and $PC_2$, are generated in the decomposition process. In such an implementation, the coefficient $a_t$ of $PC_1$ can be used to estimate the frequency of the cellular motion in a one-dimensional embodiment, i.e., in an embodiment where only the first principal component $PC_1$ is utilized. For example, referring to waveform 74 of FIG. 3, the first coefficient, $a_t$, is charted with respect to time to generate the waveform 74. That is, the changes in the first coefficient $a_t$ over time constitute the time series that is analyzed identify changes in the frequency associated with the motion of one or more treated cells 52.

In other embodiments, obviously, additional principal components, such as $PC_2$, and their respective coefficients, such as $b_t$, may be incorporated into the frequency estimation. In general, the present technique encompasses decomposing a motion signal or motion data such that one or more components generated during the decomposition can be projected into a lower dimensional space. By projecting the components of interest into a lower dimensional space, motion analysis is comparatively easier than if the analysis were performed in regular or higher dimensional space.

While the preceding discussion describes an exemplary embodiment of the present technique useful for assessing treatment effects on in vivo or in vitro cells, other implementations are also envisioned. For example, referring now to FIG. 4, exemplary acts for determining cell state (i.e., the maturity, viability, differentiation status, activation status, and so forth) based on observed cellular motion are described. In such an implementation, the cells 16, either in an in vivo state or an in vitro state, are imaged (Block 54) to acquire successive frame of a video or other successive images 56, as discussed above. Likewise, motion data 60 is generated (Block 58) and decomposed (Block 62) to generate motion components 64, as discussed above. The motion components 64 may then be used to assess (Block 80) the state of the one or more cells 16 based on the observed motion characteristics of the cells 16.

Figure 4:
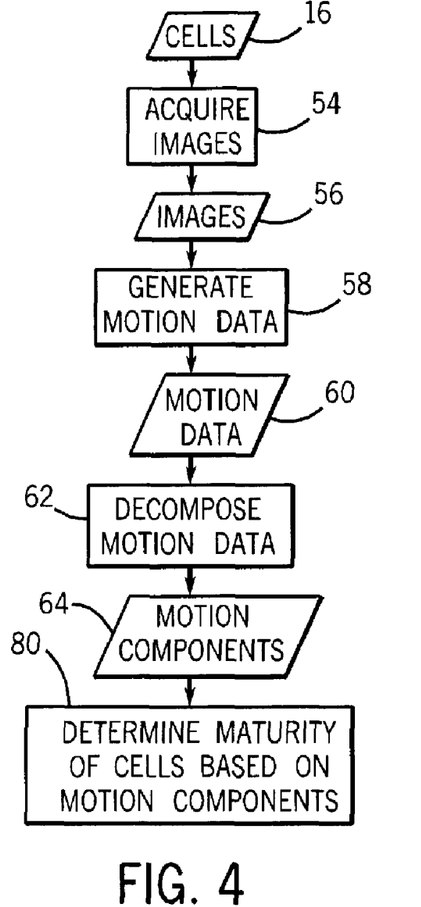
FIG. 4 is a flow chart depicting acts for determining cell maturity, in accordance with the present technique.

Such an implementation may be useful where one or more cells 16 to be used in an assay procedure, as described above, may have different degrees of maturity or differentiation and the degree of maturity or differentiation may impact the assay results. For example, in contexts where progenitor cells are cultured to form cardiomyocytes, it may be desirable to know if the cell culture consists of mature or immature cardiomyocytes. In particular, mature cardiomyocytes exhibit coordinated, rhythmic motion while the motion of immature cardiomyocytes, by contrast, is uncoordinated. In assessing the effects of an administered treatment, therefore, it is desirable to know whether the treated cells exhibited coordinated motion before the treatment or not. Indeed, a cell culture of immature cardiomyocytes may not be subjected to a treatment at all, as it may not be possible to determine the desired motion effects due to the immaturity of the cardiomyocytes. In this manner, the present technique may be used as an initial screen to determine whether cells 16 are suitable for use in an assay or screening procedure, with immature cell cultures being withheld from further treatment and screening until sufficient coordinated motion is detected to indicate the desired maturity.

Figure 5:
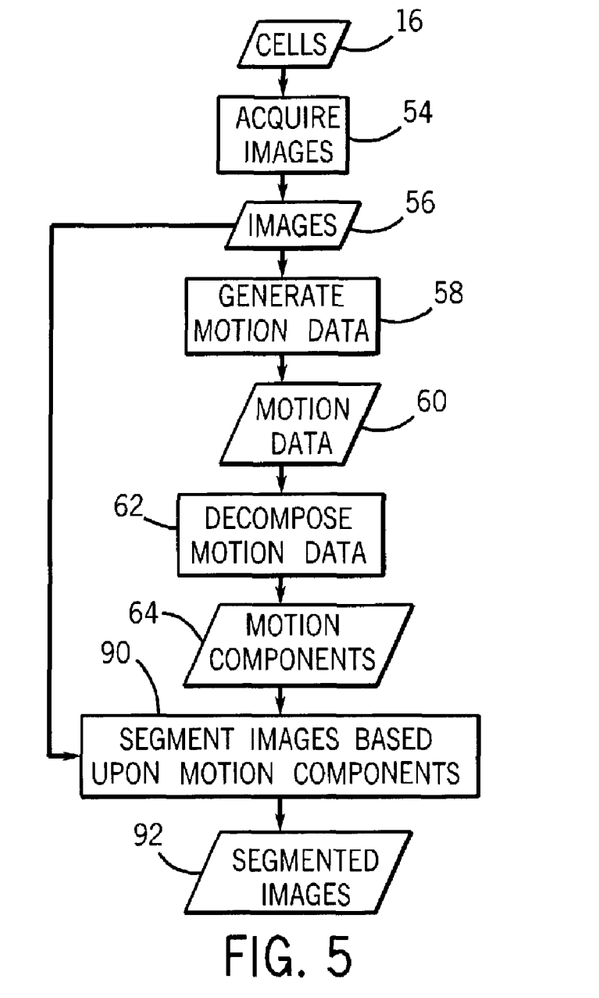
FIG. 5 is a flow chart depicting acts for segmenting an image, in accordance with the present technique.

Further, to the extent that a cell culture, such as on slab 18 (FIG. 1) may have both mature and immature cells, the present technique may be used to segment such a culture to allow use of the mature regions in an assay or screening procedure while excluding the immature regions from further analysis. Turning now to FIG. 5, exemplary acts for determining for segmenting a cell culture based on observed cellular motion are described. In such an implementation, the cells 16, either in an in vivo state or an in vitro state, are imaged (Block 54) to acquire successive frame of a video or other successive images 56, as discussed above. Likewise, motion data 60 is generated (Block 58) and decomposed (Block 62) to generate motion components 64, as discussed above. The motion components 64 may then be used to assess whether the cells 16 are mature or immature based on the observed motion characteristics of the cells 16 and to spatially segment (Block 90) the images 56 of the cell culture to generate segmented images 92 that may be differentially processed.

In this manner, the present techniques for deriving motion components may also be used to assess the differentiation and/or maturity of cells at different spatial regions of the cell culture. Based on this segmentation, the cell culture may be treated with a compound, as described above, and only those portions of the resulting images 56 that correspond to the spatial locations within the cell culture which included mature cells may be subsequently analyzed for treatment effects, i.e., the cell culture is segmented into mature and immature cells and only image data pertaining to the mature cells is analyzed.

For example, in contexts where progenitor cells are cultured to form myocytes (such as cardiomyocytes), it may be desirable to know if the entire culture of cells are at the same degree of differentiation or whether the degree of differentiation varies across the slab 18 (FIG. 1). By way of example, mature cardiomyocytes exhibit coordinated, rhythmic motion while the motion of immature cardiomyocytes, by contrast, is relatively uncoordinated. In assessing the effects of an administered treatment, therefore, it is desirable to know whether the treated cells exhibited coordinated motion before the treatment or not. The present techniques for deriving motion components may also be used to assess the coordination and/or rhythmic nature of cellular motion to determine what locations within a cell culture have mature cardiomyocytes, i.e., coordinated rhythmic motion, and which have immature cardiomyocytes, i.e., no coordinated motion. Based on this segmentation, the cell culture may be treated with a compound, as described above, and only those spatial locations within the cell culture which included mature cardiomyocytes may be subsequently analyzed for treatment effects, i.e., the cell culture is segmented into mature and immature cells and only data pertaining to the mature cells is analyzed.

As will be appreciated, though the present discussion, for simplicity, only described two categories of cells for segmentation, i.e., mature and immature, in some implementations finer gradations of cellular maturity may be assessed based on cellular motion. In such implementations, segmentation may, therefore, be with respect to more than two categories. For example, in the cardiomyocyte example, undifferentiated cells may exhibit no motion, differentiated but immature cardiomyocytes may exhibit uncoordinated motion, and mature cardiomyocytes may exhibit coordinated motion. Segmentation may therefore distinguish between these three groups, with no subsequent analysis of undifferentiated cells and separate analyses of the respective mature and immature cardiomyocytes.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for evaluating cellular motion and/or properties, comprising:

acquiring a plurality of images of a plurality of cells, wherein at least some of the cells exhibit coordinated, rhythmic motion;

deriving motion data for the plurality of cells from the plurality of images;

decomposing the motion data to generate one or more motion components; and evaluating the one or more motion components to determine which cells of the plurality of cells exhibit coordinated, rhythmic motion and which do not exhibit coordinated, rhythmic motion or to determine whether a treatment applied to the plurality of cells has altered or disrupted the coordinated, rhythmic motion exhibited by at least some of the cells.

2. The method of claim 1, comprising segmenting one or more of the plurality of images based on which cells exhibit coordinated, rhythmic motion and which do not.

3. The method of claim 1, comprising determining the state of some or all of the plurality of cells based on which cells exhibit coordinated, rhythmic motion and which do not.

4. The method of claim 1, wherein the plurality of images comprise frames of a video or a set of sequential periodic images.

5. The method of claim 1, wherein the plurality of cells comprise in-vitro cells.

6. The method of claim 5, wherein the in-vitro cells comprise at least one of progenitor cells or myocytes.

7. The method of claim 1, wherein the plurality of cells comprise in-vivo cells.

8. The method of claim 7, wherein the in-vivo cells comprise cells of at least one of a model organism, a tissue sample, or a cell culture.

9. The method of claim 1, wherein the plurality of cells comprises a single cell, a sheet or a panel of cells, or a volume of cells.

10. The method of claim 1, wherein the plurality of images are acquired under magnification.

11. The method of claim 1, wherein deriving the motion data comprises:

generating a respective displacement vector diagram representing the motion between each sequential pair of images; and analyzing the displacement vector diagrams to derive the motion data.

12. The method of claim 1, wherein deriving the motion data comprises analyzing respective vector fields representative of the motion between sequential images.

13. The method of claim 1, wherein decomposing the motion data is performed on one or more components derived using a factorization technique.

14. A computer program product provided on one or more non-transitory computer-readable media, the computer program product, when executed on a processor, performing acts comprising:

deriving motion data for a plurality of cells from a plurality of images, wherein at least some of the cells exhibit coordinated, rhythmic motion;

decomposing the motion data to generate one or more motion components; and evaluating the one or more motion components to determine which cells of the plurality of cells exhibit coordinated, rhythmic motion and which do not exhibit coordinated, rhythmic motion or to determine whether a treatment applied to the plurality of cells has altered or disrupted the coordinated, rhythmic motion exhibited by at least some of the cells.

15. The computer program product as recited in claim 14, wherein the computer program product, when executed on the processor, causes the acquisition of the plurality of images of the plurality of cells.

16. The computer program product as recited in claim 15, wherein the acquisition of the plurality of images occurs under magnification.

17. The computer program product as recited in claim 14, wherein the computer program product, when executed on the processor, segments one or more of the plurality of images based on which cells exhibit coordinated, rhythmic motion and which do not.

18. The computer program product as recited in claim 14, wherein the computer program product, when executed on the processor, determines the state of some or all of the plurality cells based on which cells exhibit coordinated, rhythmic motion and which do not.

19. The computer program product as recited in claim 14, wherein the plurality of images comprise frames of a video or a set of sequential periodic images.

20. The computer program product as recited in claim 14, wherein deriving the motion data comprises generating a respective displacement vector diagram representing the motion between each sequential pair of images and analyzing the displacement vector diagrams to derive the motion data.

21. The computer program product as recited in claim 14, wherein deriving the motion data comprises analyzing respective vector fields representative of the motion between sequential images.

22. The computer program product as recited in claim 14, wherein decomposing the motion data involves processing on one or more components derived by means of a factorization technique.

23. An image analysis system, comprising:

an imager;

data acquisition circuitry configured to acquire images of a plurality cells via the imager, wherein at least some of the cells exhibit coordinated, rhythmic motion; and data processing circuitry configured to derive motion data for the plurality of cells from the images, to decompose the motion data to generate one or more motion components, and to evaluate the one or more motion components to determine which cells of the plurality of cells exhibit coordinated, rhythmic motion and which do not exhibit coordinated, rhythmic motion or to determine whether a treatment applied to the plurality of cells has altered or disrupted the coordinated, rhythmic motion exhibited by at least some of the cells.

24. The image analysis system of claim 23, comprising system control circuitry configured to control the operation of at least one of the imager, the data acquisition circuitry, or the data processing circuitry.

25. The image analysis system of claim 23, wherein the imager is configured to magnify.

26. The image analysis system of claim 23, wherein the data processing circuitry is configured to segment the images based on which cells exhibit coordinated, rhythmic motion and which do not.

27. The image analysis system of claim 23, wherein the data processing circuitry is configured to determine the state of some or all of the plurality of cells based on which cells exhibit coordinated, rhythmic motion and which do not.

28. The image analysis system of claim 23, wherein the images comprise frames of a video or a set of sequential periodic images.

29. The image analysis system of claim 23, wherein the data processing circuitry derives the motion data by generating a respective displacement vector diagram representing the motion between each sequential pair of images and analyzes the displacement vector diagrams to derive the motion data.

30. The image analysis system of claim 23, wherein the data processing circuitry derives the motion data by analyzing respective vector fields representative of the motion between sequential images.

31. The image analysis system of claim 23, wherein the data processing circuitry decomposes the motion data by performing an operation on one or more components derived using a factorization technique.

32. The image analysis system of claim 23, wherein the plurality of cells grow in or on a medium provided as a sheet or panel or a volume.

* * * * *

UNITED STATES PATENT AND TRADEMARK OFFICE
CERTIFICATE OF CORRECTION

| | | |
|---|---|---|
| PATENT NO. | : 7,940,978 B2 | Page 1 of 1 |
| APPLICATION NO. | : 11/758531 | |
| DATED | : May 10, 2011 | |
| INVENTOR(S) | : Rittscher et al. | |

It is certified that error appears in the above-identified patent and that said Letters Patent is hereby corrected as shown below:

ON THE TITLE PAGE

Item (56), under "OTHER PUBLICATIONS", Line 4, delete "Sympos ium" and insert -- Symposium --, therefor.

On the Title page, in the Figure, for Tag "26", Line 1, delete "ACQUSITION" and insert -- ACQUISITION --, therefor.

IN THE DRAWINGS

In Fig. 1, Sheet 1 of 4, for Tag "26", Line 1, delete "ACQUSITION" and insert -- ACQUISITION --, therefor.

IN THE CLAIMS

In Column 12, Line 37, in Claim 23, delete "plurality" and insert -- plurality of --, therefor.

Signed and Sealed this
Twenty-first Day of August, 2012

David J. Kappos
*Director of the United States Patent and Trademark Office*